United States Patent
McQuillen et al.

(10) Patent No.: US 10,208,644 B2
(45) Date of Patent: Feb. 19, 2019

(54) METHODS AND SYSTEMS FOR OPERATING AN EXHAUST OXYGEN SENSOR BASED ON WATER CONTACT AT THE SENSOR

(71) Applicant: Ford Global Technologies, LLC, Dearborn, MI (US)

(72) Inventors: Michael McQuillen, Warren, MI (US); Gopichandra Surnilla, West Bloomfield, MI (US); Daniel A. Makled, Dearborn, MI (US); Richard E. Soltis, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 155 days.

(21) Appl. No.: 15/346,387

(22) Filed: Nov. 8, 2016

(65) Prior Publication Data
US 2018/0128149 A1   May 10, 2018

(51) Int. Cl.
| | |
|---|---|
| *F01N 11/00* | (2006.01) |
| *F02D 41/00* | (2006.01) |
| *F02D 41/14* | (2006.01) |
| *G01N 27/407* | (2006.01) |

(52) U.S. Cl.
CPC .......... *F01N 11/007* (2013.01); *F02D 41/005* (2013.01); *F02D 41/0077* (2013.01); *F02D 41/1454* (2013.01); *G01N 27/407* (2013.01); *F01N 2560/025* (2013.01); *F01N 2560/028* (2013.01); *F01N 2900/1628* (2013.01); *F02D 41/1456* (2013.01); *F02D 2041/1472* (2013.01)

(58) Field of Classification Search
CPC ............. F01N 11/007; F01N 2560/025; F01N 2560/028; F02D 41/1456; F02D 41/222; F02D 2041/1472; G01N 27/419
See application file for complete search history.

(56) References Cited

U.S. PATENT DOCUMENTS

| | | | |
|---|---|---|---|
| 9,309,838 B2 | 4/2016 | Surnilla et al. | |
| 2008/0172167 A1* | 7/2008 | Ootake | .................. F01N 3/106 701/103 |
| 2015/0076134 A1 | 3/2015 | Surnilla et al. | |
| 2015/0192084 A1* | 7/2015 | Surnilla | ................ F02D 41/123 123/674 |

* cited by examiner

*Primary Examiner* — Jonathan Matthias
(74) *Attorney, Agent, or Firm* — Julia Voutyras; McCoy Russell LLP

(57) ABSTRACT

Methods and systems are provided for operating an exhaust oxygen sensor coupled to an exhaust passage of an internal combustion engine in response to detecting water at the sensor. In one example, a method may include indicating water at an exhaust oxygen sensor positioned in an engine exhaust passage based on a sensor parameter of the exhaust oxygen sensor while operating the exhaust oxygen sensor in a variable voltage (VVs) mode where a reference voltage is adjusted from a lower, first voltage to a higher, second voltage; and adjusting one or more of sensor operation and engine operation based on the indicating water.

17 Claims, 4 Drawing Sheets

METHODS AND SYSTEMS FOR OPERATING AN EXHAUST OXYGEN SENSOR BASED ON WATER CONTACT AT THE SENSOR

FIELD

The present description relates generally to methods and systems for operating an exhaust oxygen sensor coupled to an exhaust passage of an internal combustion engine in response to water detection at the sensor.

BACKGROUND/SUMMARY

Engine systems may utilize one or more gas constituent sensors, such as oxygen sensors, for sensing an oxygen concentration of air flowing through engine air passages. In one example, an engine system may include one or more intake oxygen sensors (IAO2) located in the engine intake. For example, an intake oxygen sensor may be positioned in an intake passage, downstream from a compressor and a charge air cooler, to provide an indication of EGR flow. In another example, the engine system may include one or more exhaust gas sensors in an exhaust system of the engine system to detect an air-fuel ratio of exhaust gas exhausted from the engine. Under certain engine operating conditions, such as a cold start or condensate formation, water may splash against and contact the oxygen sensor. When water contacts the oxygen sensor, the temperature of the sensor begins to decrease. As a result, heater power of a heating element of the oxygen sensor increases to increase the sensor temperature. When the heater power increases for an extended period of time when water is on the oxygen sensor, the heating element may crack, thereby degrading the oxygen sensor.

Other attempts to address degradation of the oxygen sensor due to water contacting the sensor include adjusting a heating power of a heating element of the oxygen sensor. One example approach is shown by Surnilla et. al. in US 2015/0076134. Therein, the heater power of the heating element of an oxygen sensor is adjusted in response to an increase in the heater power by a threshold amount. As an example, a baseline power level of the oxygen sensor is determined during a condition wherein no water is contacting the sensor. When heater power increases above the baseline power level (e.g., due to water splashing on the sensor), the heating power may be decreased by turning off power of a heating element of the sensor. After a certain duration, the heater power may be turned back on and increased to baseline power level. In this way, reducing the heater power when water is indicated at the oxygen sensor may reduce oxygen sensor degradation via cracking of the heating element.

However, the inventors herein have recognized potential issues with such systems. For example, turning off the heater power to the heating element when water is indicated on the sensor, and then turning the heater back on after a certain time leads to fluctuations in the temperature of the sensor. As such, the fluctuations in the sensor temperature may adversely affect the ability of the sensor to sense oxygen concentration in the exhaust. In addition, the output of the sensor during such conditions may be inaccurate, thereby affecting air fuel control and hence affecting the performance of the engine.

In one example, the issues described above may be addressed by a method for an engine method, comprising indicating water at an exhaust oxygen sensor positioned in an engine exhaust passage based on a sensor parameter of the exhaust oxygen sensor while operating the exhaust oxygen sensor in a variable voltage (VVs) mode where a reference voltage is adjusted from a lower, first voltage to a higher, second voltage, and adjusting one or more of sensor operation and engine operation based on the indicating water. In this way, sensor degradation may be reduced.

As an example, the exhaust oxygen sensor may be traditionally operated in a non-VVs mode wherein the sensor is operated at the lower voltage, and an output of the exhaust oxygen sensor may be used for determining an air-fuel-ratio (AFR). As such, water at the exhaust oxygen sensor may be detected based on the sensor parameter such as a pumping current or change in pumping current of the exhaust oxygen sensor. For example, when the pumping current of the sensor falls below a threshold current, water splash on the sensor may be indicated. In another example, if the change in pumping current is higher than a baseline change in pumping current (e.g., when no water is present on the sensor), then water splash on the sensor may be indicated. When water splash on the sensor is indicated, the exhaust oxygen sensor may no longer be used as a traditional air-fuel sensor; instead, the sensor may be transitioned from the non-VVs mode to the VVs mode, where the sensor is operated at the higher voltage and/or modulated between the lower voltage and higher voltage. While the exhaust oxygen sensor is not operated as the traditional air-fuel sensor, AFR may be estimated using a different, downstream sensor, and/or using previously determined AFR. In this way, air fuel control may not be affected while the exhaust oxygen sensor is being operated in the VVs mode.

Additionally, the sensor parameters may be checked continuously while the sensor is in VVs mode to determine when water has evaporated from the exhaust oxygen sensor. For example, once the change in pumping current reaches the baseline change in pumping current, then the exhaust oxygen sensor is considered "dry", and the sensor may then be transitioned back to the non-VVs mode. Once the exhaust oxygen sensor is in the non-VVs mode, the sensor may be used to determine AFR. In this way, sensor degradation may be reduced, and the integrity of the exhaust oxygen sensor may be maintained. Further, an accuracy of AFR estimates based on the exhaust oxygen sensor output may be increased, thereby increasing engine efficiency.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
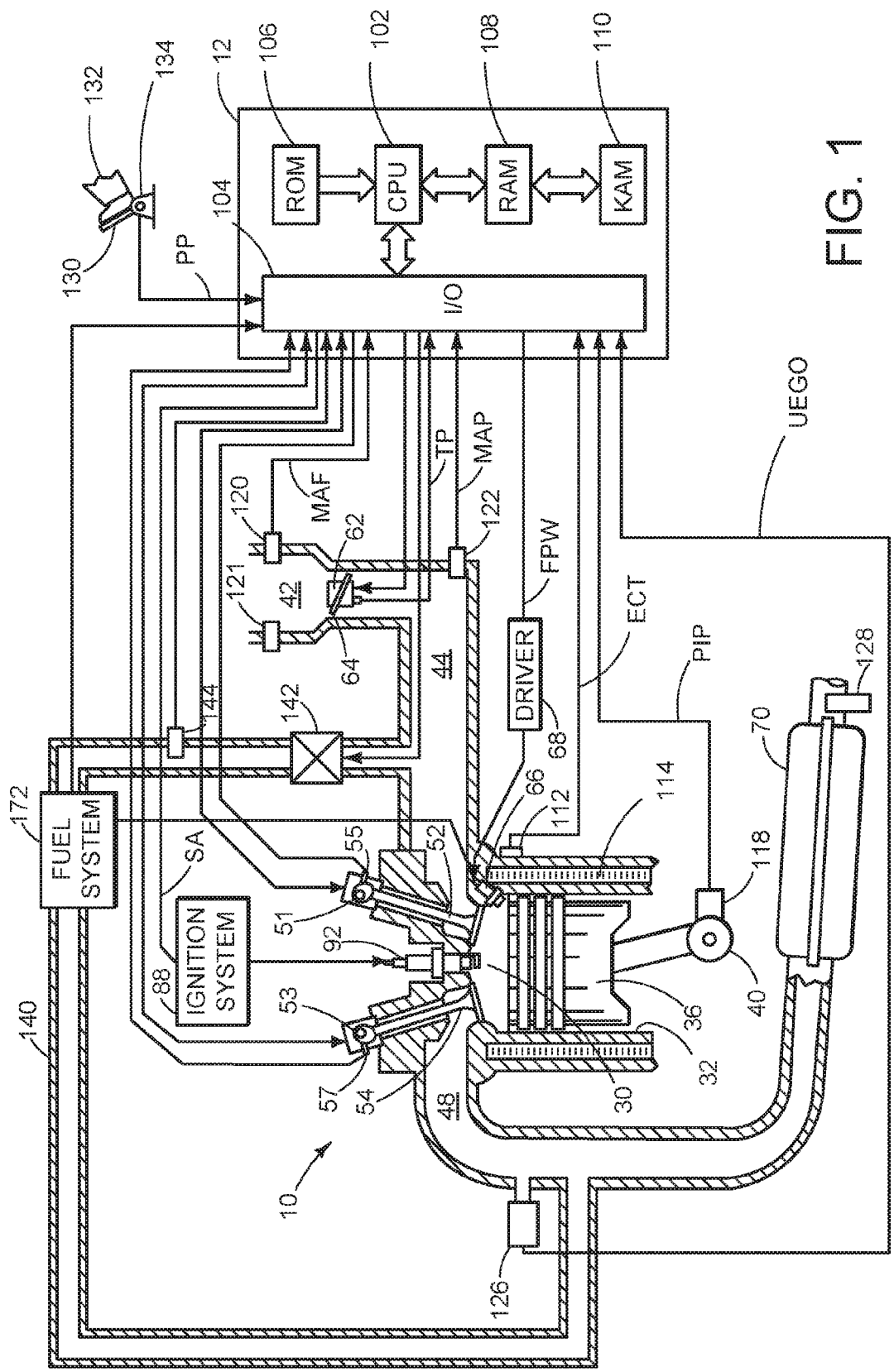
FIG. 1 shows a schematic diagram of an engine including an exhaust system and an exhaust oxygen sensor.
Figure 2:
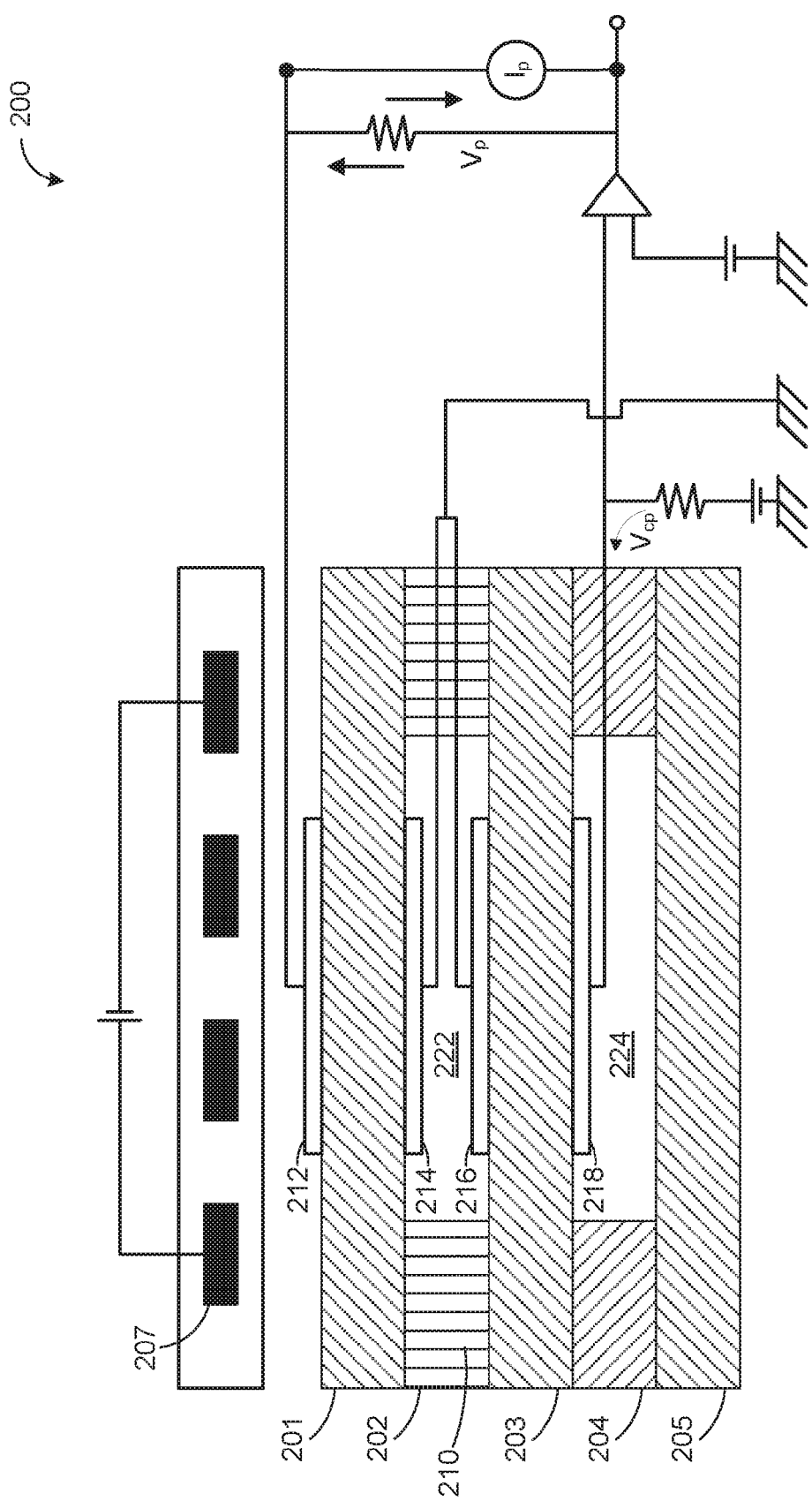
FIG. 2 shows a schematic diagram illustrating the exhaust oxygen sensor capable of operating in each of a reference mode or a non-variable voltage mode (VVs) and a VVs mode.
Figure 3:
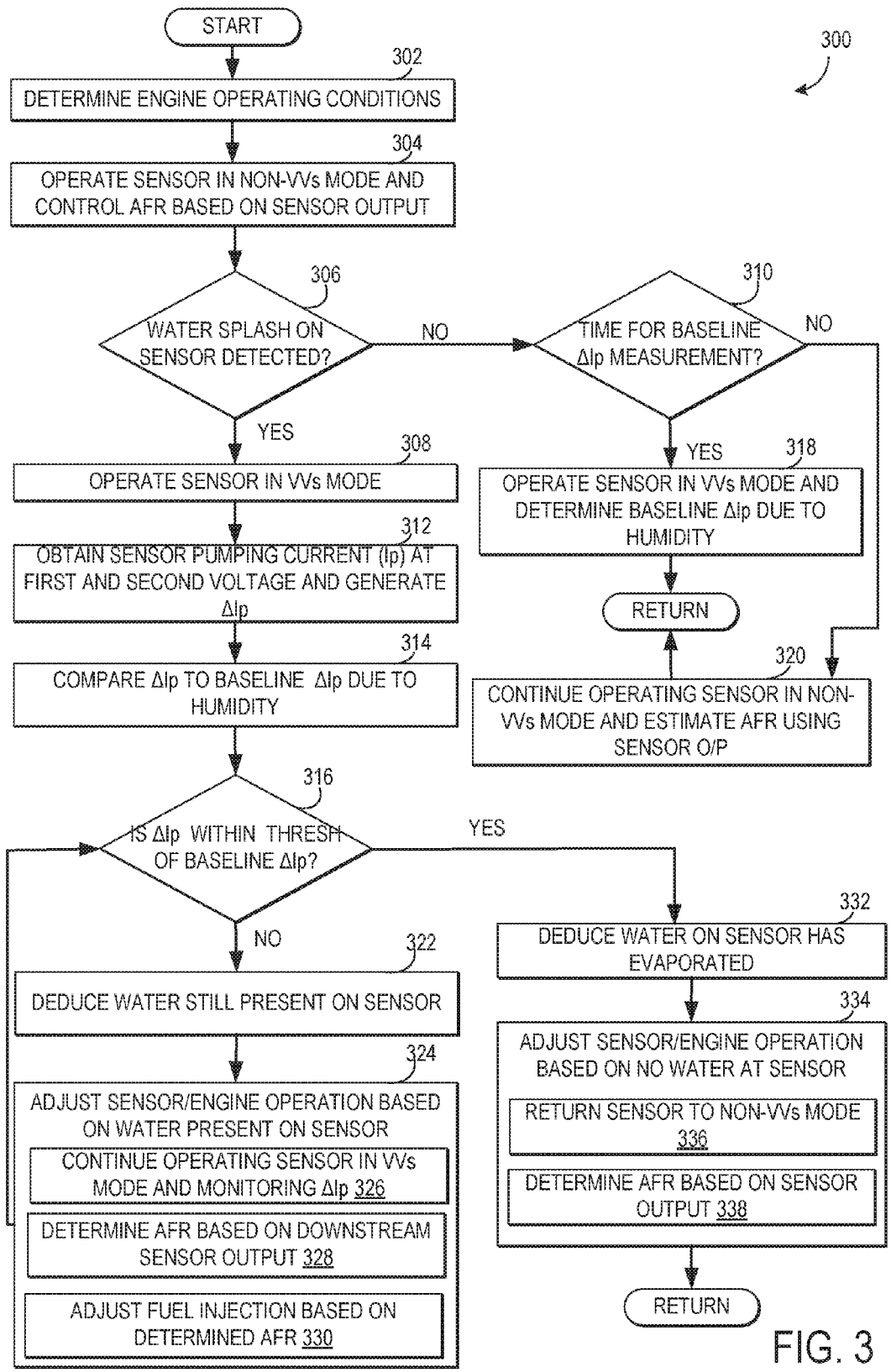
FIG. 3 shows a flow chart illustrating an example method for operating the exhaust oxygen sensor in the VVs mode in response to detecting water at the exhaust oxygen sensor.
Figure 4:
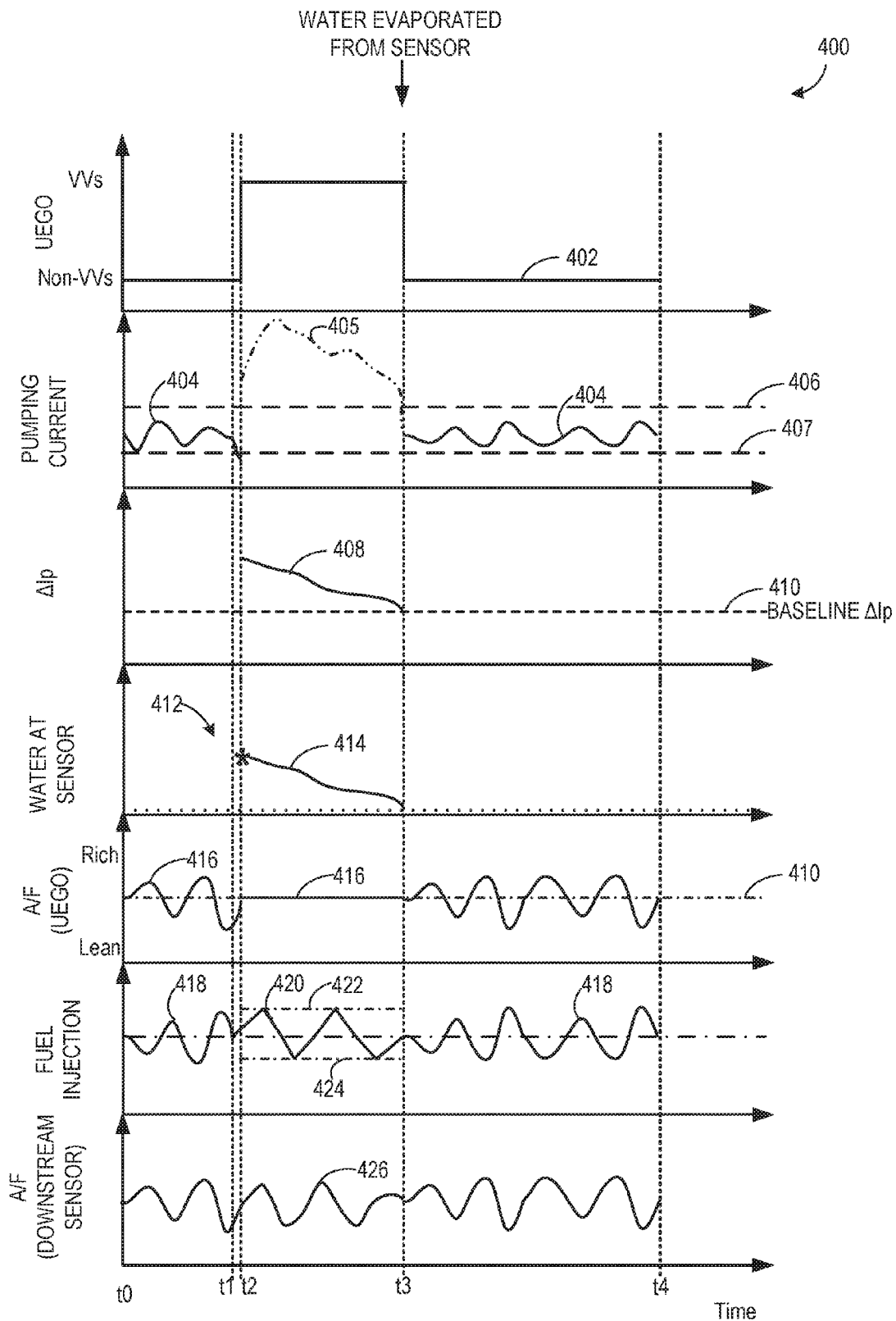
FIG. 4 shows an example relationship between modes of operation of the exhaust oxygen sensor, a pumping current output of the exhaust oxygen sensor, a change in baseline pumping current, an air-fuel ratio control, and a fuel injection profile.

The following description relates to systems and methods for operating an exhaust oxygen sensor in response to water splash at the sensor, such as the oxygen sensor shown in FIGS. 1-2 (referred to herein as an exhaust oxygen sensor). An engine controller may be configured to perform a control routine, such as the example method of FIG. 3 to determine if water has splashed on the exhaust oxygen sensor, and accordingly transition the sensor from a non-VVs mode to a VVs mode. As such, the sensor may be normally operated in the non-VVs mode to estimate air-fuel-ratio (AFR), and transitioned to the VVs mode only if water is splashed on the sensor. An example relationship between modes of operation of the exhaust oxygen sensor, a pumping current output of the exhaust oxygen sensor, a change in baseline pumping current, an air-fuel ratio control, and a fuel injection profile is shown in FIG. 4. While the exhaust oxygen sensor is operated in the VVs mode, the controller may adjust fuel injection to the engine cylinders based on an output of a different, downstream sensor (FIG. 4). Once water has evaporated from the exhaust oxygen sensor, the sensor may be returned to the non-VVs mode and subsequently used to estimate AFR. In this way, by transitioning the sensor to the VVs mode when water splashes on the sensor, sensor degradation may be reduced. Additionally, by using the downstream sensor to estimate AFR while water is present on the exhaust oxygen sensor, stoichiometric operation of the cylinders may be maintained.

Referring now to FIG. 1, a schematic diagram showing one cylinder of multi-cylinder engine 10, which may be included in a propulsion system of an automobile, is illustrated. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 44 via intake passage 42 and may exhaust combustion gases via exhaust passage 48. Intake manifold 44 and exhaust passage 48 can selectively communicate with combustion chamber 30 via respective intake valve 52 and exhaust valve 54. In some embodiments, combustion chamber 30 may include two or more intake valves and/or two or more exhaust valves.

In this example, intake valve 52 and exhaust valves 54 may be controlled by cam actuation via respective cam actuation systems 51 and 53. Cam actuation systems 51 and 53 may each include one or more cams and may utilize one or more of cam profile switching (CPS), variable cam timing (VCT), variable valve timing (VVT), and/or variable valve lift (VVL) systems that may be operated by controller 12 to vary valve operation. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

In some embodiments, each cylinder of engine 10 may be configured with one or more fuel injectors for providing fuel thereto. As a non-limiting example, cylinder 30 is shown including one fuel injector 66. Fuel injector 66 is shown coupled directly to cylinder 30 for injecting fuel directly therein in proportion to the pulse width of signal FPW received from controller 12 via electronic driver 68. In this manner, fuel injector 66 provides what is known as direct injection (hereafter also referred to as "DI") of fuel into combustion cylinder 30.

It will be appreciated that in an alternate embodiment, injector 66 may be a port injector providing fuel into the intake port upstream of cylinder 30. It will also be appreciated that cylinder 30 may receive fuel from a plurality of injectors, such as a plurality of port injectors, a plurality of direct injectors, or a combination thereof.

Fuel tank in fuel system 172 may hold fuels with different fuel qualities, such as different fuel compositions. These differences may include different alcohol content, different octane, different heats of vaporization, different fuel blends, and/or combinations thereof etc. The engine may use an alcohol containing fuel blend such as E85 (which is approximately 85% ethanol and 15% gasoline) or M85 (which is approximately 85% methanol and 15% gasoline). Alternatively, the engine may operate with other ratios of gasoline and ethanol stored in the tank, including 100% gasoline and 100% ethanol, and variable ratios there between, depending on the alcohol content of fuel supplied by the operator to the tank. Moreover, fuel characteristics of the fuel tank may vary frequently. In one example, a driver may refill the fuel tank with E85 one day, and E10 the next, and E50 the next. As such, based on the level and composition of the fuel remaining in the tank at the time of refilling, the fuel tank composition may change dynamically.

The day-to-day variations in tank refilling can thus result in frequently varying fuel composition of the fuel in fuel system 172, thereby affecting the fuel composition and/or fuel quality delivered by injector 66. The different fuel compositions injected by injector 166 may herein be referred to as a fuel type. In one example, the different fuel compositions may be qualitatively described by their research octane number (RON) rating, alcohol percentage, ethanol percentage, etc.

It will be appreciated that while in one embodiment, the engine may be operated by injecting the variable fuel blend via a direct injector, in alternate embodiments, the engine may be operated by using two injectors and varying a relative amount of injection from each injector. It will be further appreciated that when operating the engine with a boost from a boosting device such as a turbocharger or supercharger (not shown), the boosting limit may be increased as an alcohol content of the variable fuel blend is increased. In one embodiment, an exhaust gas sensor 126 coupled to an exhaust passage 48 may be operated in a variable voltage (VVs) mode (FIG. 2) to estimate an amount of alcohol in the fuel injected to the engine (e.g., a fuel ethanol content estimation as shown in FIG. 7).

Continuing with FIG. 1, intake passage 42 may include a throttle 62 having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12. In one embodiment, the intake passage 42 may additionally include a humidity sensor 121 for measuring ambient humidity. In another embodiment, the humidity sensor 121 may additionally or alternatively be placed in the exhaust passage 48.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

The exhaust gas sensor 126 (e.g., exhaust oxygen sensor) is shown coupled to the exhaust passage 48 upstream of emission control device 70. Hereafter, the exhaust gas sensor 126 may be interchangeably referred to as exhaust oxygen sensor or exhaust sensor or sensor. Exhaust gas sensor 126 may be any suitable sensor for providing an indication of exhaust gas air-fuel ratio (AFR) such as a linear oxygen sensor or UEGO (universal or wide-range exhaust gas oxygen), a two-state oxygen sensor or EGO, a HEGO (heated EGO), a NOx, HC, or CO sensor.

Further, in the disclosed embodiments, an exhaust gas recirculation (EGR) system may route a desired portion of exhaust gas from exhaust passage 48 to intake passage 44 via EGR passage 140. The amount of EGR provided to intake passage 44 may be varied by controller 12 via EGR valve 142. Further, an EGR sensor 144 may be arranged within the EGR passage and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

The exhaust gas sensor 126 may be normally operated in a non-variable voltage mode (also referred to as a reference mode) for measuring air-fuel ratio (AFR). In some examples, an additional sensor 128 positioned downstream of an emission control device 70 may be used to estimate AFR. As such, the emission control device 70 is shown arranged along exhaust passage 48 downstream of exhaust gas sensor 126. Device 70 may be a three way catalyst (TWC), NOx trap, various other emission control devices, or combinations thereof. In some embodiments, during operation of engine 10, emission control device 70 may be periodically reset by operating at least one cylinder of the engine within a particular air/fuel ratio.

The sensor 128 may be a linear oxygen sensor or UEGO, a two-state oxygen sensor or EGO, a HEGO (heated EGO), a NOx, HC, or CO sensor. In one example, the sensor 128 may be used in addition to the exhaust oxygen sensor 126 to determine AFR. Hereafter, the sensor 128 may be interchangeably referred to as the downstream sensor. In another example, the downstream sensor 128 may be used instead of the exhaust oxygen sensor 126 to determine AFR. For example, when water splashes on the exhaust oxygen sensor, some of the water may enter the sensor cavity. The inventors have recognized that if the exhaust oxygen sensor is incorrectly controlled when water is still present on the sensor, then it may degrade the exhaust oxygen sensor. Thus, to reduce sensor degradation, the exhaust oxygen sensor may be operated in a VVs mode. In the VVs mode, the exhaust oxygen sensor is operated between (e.g., modulated between and/or transitioned from the lower to the higher voltage) the lower voltage and a higher voltage (as described further below with reference to FIG. 2). When the exhaust oxygen sensor 126 is operated in the VVs mode (e.g., until water has evaporated from the exhaust oxygen sensor 126), AFR may not be estimated using the exhaust oxygen sensor 126; instead AFR may be estimated using a different sensor (e.g., downstream sensor 128), for example, as illustrated in FIGS. 2 and 3. In example embodiments when the system does not include additional downstream sensors, fuel injection may be adjusted based on AFR determined previously using the exhaust oxygen sensor 126, as illustrated in FIG. 3.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; and absolute manifold pressure signal, MAP, from sensor 122. Engine speed signal, RPM, may be generated by controller 12 from signal PIP. The controller 12 receives signals from the aforementioned sensors and employs various actuators of FIG. 1 to adjust engine operation based on the received signals and instructions stored on a memory of the controller.

As one example, the controller may measure a degree of richness and leanness of the air-fuel ratio (AFR) based one or more sensors such as exhaust oxygen sensor 126 and downstream sensor 128, and may accordingly adjust an amount of fuel injected to the cylinders to maintain stoichiometric operation. For example, the controller may operate the exhaust gas sensor 126 in a non-VVs mode at a lower voltage to estimate the AFR. Based on the estimated AFR, the controller may adjust a pulse width signal delivered to the fuel injector (e.g., fuel injector 66) to adjust an amount of fuel delivered via the fuel injector to maintain overall stoichiometric engine operation.

However, when water splashes on (or is present on) the exhaust oxygen sensor 126, the controller may transition the exhaust oxygen sensor 126 from the non-VVs mode to VVs mode by increasing the operating voltage of the sensor from the lower voltage to a higher voltage. For example, the controller may deduce that water is splashed on the sensor based on a change in one or more of a heater power, a pumping current, and/or a change in pumping current of the exhaust oxygen sensor. As an example, if the pumping current of the exhaust oxygen sensor falls below a first threshold current, the controller may deduce that water has splashed on the sensor. Upon determining that water is splashed on the sensor, the controller may stop operating the sensor in the non-VVs mode, and further transition the sensor to the VVs mode. By operating the sensor in the VVs mode at the higher voltage (and/or modulating the sensor between the lower and higher voltage), the controller may monitor the output of the sensor and determine when water has evaporated from the sensor. For example, the controller may determine that water has evaporated from the sensor when the pumping current rises above a second threshold current. As such, the controller may set the first threshold current based on no water being present on the exhaust oxygen sensor, and further set the second threshold based water being present on the exhaust oxygen sensor. When water has evaporated from the exhaust oxygen sensor, the controller may transition the sensor to the non-VVs mode by operating the sensor in the lower voltage.

As another example, the controller may operate the exhaust oxygen sensor in the non-VVs mode to determine ambient humidity based on a baseline change in pumping current ($\Delta$Ip) of the exhaust oxygen sensor. For example, the controller may transition the sensor from non-VVs mode to VVs mode to estimate an amount of water in the exhaust gas due to ambient humidity when water is not present on the exhaust oxygen sensor, and then return the sensor back to non-VVs mode once the estimation is complete. As such, the amount of water estimated using the exhaust oxygen sensor in the VVs mode when no water on present on the sensor may be a baseline measurement that accounts for water due to humidity and/or additional constituents (such as fuel alcohol content) in the exhaust gas. Therefore, the baseline water (or ambient humidity) measurement represents the water that is normally present during engine operation and this is used to compare to the sensor output when water is detected on the sensor, as described with reference to FIG. 3. The estimated water amount in the exhaust due to ambient humidity may be stored in memory and may be retrieved later for the estimation of a change in pumping current comparison. When water splashes on the sensor, the controller may operate the sensor in the VVs mode, and compare the change in pumping current of the sensor with the baseline $\Delta$Ip to determine if water is present on the sensor, as explained with reference to FIG. 3. When the exhaust oxygen sensor is operated in the VVs mode, the controller may estimate AFR from other sensors positioned in the engine systems (e.g., sensor 128), or use a predetermined AFR estimate to adjust fuel injection. In this way, the controller may selectively adjust the operation of the exhaust oxygen sensor when water splashes on the sensor and reduce sensor degradation. The non-VVs mode and VVs mode of operation of the exhaust oxygen sensor is described with reference to FIG. 2.

Storage medium read-only memory 106 can be programmed with computer readable data representing instructions executable by processor 102 for performing the methods described below as well as other variants that are anticipated but not specifically listed.

As described above, FIG. 1 shows only one cylinder of a multi-cylinder engine, and each cylinder may similarly include its own set of intake/exhaust valves, fuel injector, spark plug, etc.

Next, FIG. 2 shows a schematic view of an example embodiment of a UEGO sensor 200 configured to measure a concentration of oxygen (O2) in an exhaust gas stream. Sensor 200 may operate as exhaust gas sensor 126 of FIG. 1, for example. Sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted UEGO sensor is formed from five ceramic layers, it will be appreciated that the UEGO sensor may include other suitable numbers of ceramic layers.

Layer 202 includes a material or materials creating a diffusion path 210. Diffusion path 210 is configured to introduce exhaust gases into a first internal cavity 222 via diffusion. Diffusion path 210 may be configured to allow one or more components of exhaust gases, including but not limited to a desired analyte (e.g., O2), to diffuse into internal cavity 222 at a more limiting rate than the analyte can be pumped in or out by pumping electrodes pair 212 and 214. In this manner, a stoichiometric level of O2 may be obtained in the first internal cavity 222.

Sensor 200 further includes a second internal cavity 224 within layer 204 separated from the first internal cavity 222 by layer 203. The second internal cavity 224 is configured to maintain a constant oxygen partial pressure equivalent to a stoichiometric condition, e.g., an oxygen level present in the second internal cavity 224 is equal to that which the exhaust gas would have if the air-fuel ratio was stoichiometric. The oxygen concentration in the second internal cavity 224 is held constant by pumping voltage, Vcp. Herein, second internal cavity 224 may be referred to as a reference cell.

A pair of sensing electrodes 216 and 218 is disposed in communication with first internal cavity 222 and reference cell 224. The sensing electrodes pair 216 and 218 detects a concentration gradient that may develop between the first internal cavity 222 and the reference cell 224 due to an oxygen concentration in the exhaust gas that is higher than or lower than the stoichiometric level. A high oxygen concentration may be caused by a lean exhaust gas mixture, while a low oxygen concentration may be caused by a rich mixture.

A pair of pumping electrodes 212 and 214 is disposed in communication with internal cavity 222, and is configured to electrochemically pump a selected gas constituent (e.g., O2) from internal cavity 222 through layer 201 and out of sensor 200. Alternatively, the pair of pumping electrodes 212 and 214 may be configured to electrochemically pump a selected gas through layer 201 and into internal cavity 222. Herein, pumping electrodes pair 212 and 214 may be referred to as an O2 pumping cell.

Electrodes 212, 214, 216, and 218 may be made of various suitable materials. In some embodiments, electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into internal cavity 222 includes applying a voltage Vp (e.g., reference voltage) across pumping electrode pair 212 and 214. The pumping voltage Vp applied to the O2 pumping cell pumps oxygen into or out of first internal cavity 222 in order to maintain a stoichiometric level of oxygen in the cavity pumping cell. The resulting pumping current Ip is proportional to the concentration of oxygen in the exhaust gas. A control system (not shown in FIG. 2) generates the pumping current signal Ip as a function of the intensity of the applied pumping voltage Vp required to maintain a stoichiometric level within the first internal cavity 222. Thus, a lean mixture will cause oxygen to be pumped out of internal cavity 222 and a rich mixture will cause oxygen to be pumped into internal cavity 222.

It should be appreciated that the UEGO sensor described herein is merely an example embodiment of a UEGO sensor, and that other embodiments of UEGO sensors may have additional and/or alternative features and/or designs. The oxygen sensor of FIG. 2 may be a variable voltage oxygen sensor configured to operate at a first, lower voltage (e.g., reference voltage) where water molecules are not dissociated and a second, higher voltage (e.g., reference voltage) where water molecules are fully dissociated. As such, the second voltage is higher than the first voltage. Thus, the exhaust oxygen sensor may operate as a traditional oxygen sensor (e.g., air-fuel sensor), at only the lower, first reference voltage (e.g., approximately 450 mV). This lower voltage may be referred to herein as the base reference voltage. Said another way, the UEGO may be operated as an air-fuel sensor in order to determine an exhaust air-fuel ratio.

The sensor may be operated in VVs mode to determine an estimate of ambient humidity. As such, the ambient humidity (e.g., absolute humidity of the fresh air surrounding the vehicle) may be determined based on the first pumping current and the second pumping current (or the correction first and second pumping current). For example, the first pumping current may be subtracted from the second pumping current to obtain a change in pumping current indicative of the amount of oxygen from dissociated water molecules (e.g., the amount of water) in the sample gas. This value may be proportional to the ambient humidity and/or additional constituents within the exhaust gas. Herein, this value may be referred to as baseline change in pumping current. When water splashes on the exhaust oxygen sensor, the change in pumping current output by the exhaust oxygen sensor may be used to estimate the excess water, in addition to humidity and/or additional constituents in the exhaust gas (e.g., by comparing with the baseline change in pumping current), on the exhaust oxygen sensor.

Thus, the systems of FIGS. 1-2 provide for a system for an engine comprising an exhaust oxygen sensor coupled to an exhaust passage of the engine, and a controller including computer readable instructions for: during operation of the exhaust oxygen sensor in a reference mode where a reference voltage of the exhaust oxygen sensor is maintained at a lower, first voltage, detecting a water splash event based on a first pumping current of the exhaust oxygen sensor falling below a first threshold current. Additionally or alternatively, the controller may include instructions for transitioning the exhaust oxygen sensor to a variable voltage (VVs) mode where the reference voltage is modulated between the first voltage and a higher, second voltage, and maintaining operation in the VVs mode until a second pumping current of the exhaust oxygen sensor falls below a second threshold current. Additionally or alternatively, the first threshold current may be based on a first output of the exhaust oxygen sensor in the reference mode when no water is present on the exhaust oxygen sensor, and the second threshold may be based on a second output of the exhaust oxygen sensor in the VVs mode when water is present on the exhaust oxygen sensor. Additionally or alternatively, the second threshold current may be higher than the first threshold current. Additionally or alternatively, the controller may include instructions for estimating an air-fuel ratio when operating the exhaust oxygen sensor in the reference mode. Additionally or alternatively, the controller may include instructions for estimating ambient humidity when operating the exhaust oxygen sensor in the VVs mode.

Turning to FIG. 3, a method 300 is shown for adjusting engine operation based on an output of an exhaust oxygen sensor. Specifically, a sensor parameter of the exhaust oxygen sensor (e.g., pumping current, heater power, change in pumping current, and the like) may be monitored to determine if water has splashed on (or is present on) the exhaust oxygen sensor. When water is indicated at the exhaust oxygen sensor, the sensor is transitioned from the non-VVs mode to VVs mode where it is maintained until water has evaporated from the exhaust oxygen sensor, as described below.

As described above, an exhaust oxygen sensor (such as exhaust gas sensor 126 shown in FIG. 1 and sensor 200 shown in FIG. 2) may be a VVs sensor operable at a lower, base voltage and at a higher, target voltage. As such, the exhaust oxygen sensor may operate as a traditional air-fuel sensor where the reference voltage of the sensor is maintained at the lower, base voltage (e.g., approximately 450 mV) where water and carbon dioxide molecules are not dissociated at the sensor (referred to herein as non-VVs operation). Then, under select conditions (as explained below), the reference voltage of the exhaust oxygen sensor may be increased from the lower, base voltage (e.g., first voltage) to a higher, target voltage (e.g., second voltage) where water molecules and/or carbon dioxide molecules are dissociated. In one example, the second voltage may be in a range of approximately 900-1100 mV.

Instructions for carrying out method 300 may be executed by a controller based on instructions stored on a memory of the controller and in conjunction with signals received from sensors of the engine system, such as the sensors described above with reference to FIGS. 1 and 2. The controller may employ engine actuators of the engine system to adjust engine operation, according to the methods described below.

Method 300 begins at 302 by estimating and/or measuring engine operating conditions. Engine operating conditions may include engine speed and/or load, engine temperature, exhaust air-fuel ratio, ambient humidity, ambient temperature, mass air flow rate, exhaust gas recirculation (EGR) flow, exhaust oxygen sensor temperature, a pumping current of an exhaust oxygen sensor, a change in pumping current of the exhaust oxygen sensor, a heater power of the exhaust oxygen sensor, a temperature of the exhaust oxygen sensor, etc.

At 304, method 300 includes operating the exhaust oxygen sensor in the non-VVs mode and controlling AFR based on an output of the sensor in non-VVs mode (or reference mode). As such, operating the exhaust oxygen sensor in the non-VVs mode includes operating the exhaust oxygen sensor at a lower, first voltage (e.g., approximately 450 mV). The controller may determine AFR based on the exhaust oxygen sensor reading, and accordingly adjust fuel injection to one or more cylinders (such as cylinder 30 of FIG. 1) in response to the determined AFR.

For example, the controller may determine a control signal to send to the fuel injector actuator, such as a pulse width of the signal, being determined based on a determination of the AFR. The AFR may be based on the exhaust oxygen sensor reading when no water is detected on the sensor. The controller may determine the pulse width through a determination that directly takes into account a determined AFR, such as increasing the pulse width with when the determined AFR is leaner than stoichiometry. The controller may alternatively determine the pulse width based on a calculation using a look-up table with the input being AFR and the output being pulse-width.

In another example, the controller may estimate AFR based outputs from one or more sensors coupled to the exhaust passage. For example, a second, downstream exhaust gas sensor (such as exhaust oxygen sensor 128 shown in FIG. 1) may be coupled to an exhaust passage (such as exhaust passage 48 shown in FIG. 1) downstream of an emissions control device (such as emission control device 70 shown in FIG. 1). As such, the downstream sensor may be any suitable sensor for providing an indication of exhaust gas air-fuel ratio such as a UEGO, EGO, HEGO, etc.

In one embodiment, downstream sensor is an EGO configured to indicate the relative enrichment or enleanment of the exhaust gas after passing through the catalyst. As such, the EGO may provide output in the form of a switch point, or the voltage signal at the point at which the exhaust gas switches from lean to rich.

The controller may estimate AFR based on one or more of the exhaust oxygen sensor and the downstream sensor. Based on the estimated AFR, the controller may adjust fuel injection to the cylinders to maintain stoichiometric operation. As an example, the controller may estimate an AFR based on an average of the AFR estimated from the upstream exhaust oxygen sensor and the downstream sensor. In another example, the controller may use the AFR estimated from the downstream sensor as a correction factor to the AFR estimated from the exhaust oxygen sensor, and apply the corrected AFR for air-fuel control. In yet another example, the exhaust oxygen sensor may provide feedback to adjust the AFR near stoichiometry, and the downstream sensor may provide feedback to bias the AFR richer or leaner to enhance catalyst efficiency. In further examples, the upstream exhaust oxygen sensor may be operated in a manner to control an inner loop of the AFR and the downstream oxygen sensor (e.g., HEGO) may be operated in a manner to control an outer loop of the AFR. Herein, the output of the downstream sensor may be used to apply minor corrections to the AFR ratio measurement made by the exhaust oxygen sensor. In this way, a proper rich vs. lean state of the catalyst may be maintained.

At 306, method 300 includes determining if water has splashed on the exhaust oxygen sensor. Under certain engine operating conditions, such as during a cold start or when condensate forms in the exhaust, water may splash against and contact the exhaust oxygen sensor. Water splashing on the exhaust oxygen sensor can result in water droplets entering the sensor cavity and directly contacting the sensor cell. Continuing to operate the exhaust oxygen sensor in the non-VVs mode after water has splashed on the sensor can lead to sensor degradation. To reduce sensor degradation, the controller may monitor the sensor to detect water splash events, and accordingly modify operation of the exhaust oxygen sensor as described below. Herein, the method includes indicating water at the exhaust oxygen sensor positioned in the engine exhaust passage based on a sensor parameter (e.g., pumping current, sensor temperature, heater power, etc.), as described below.

For example, the controller may monitor a heater (such as heater 207 of sensor 200 shown in FIG. 2) of the exhaust oxygen sensor. If water splashes on the exhaust oxygen sensor and enters the sensor cell, water may contact the heater. When water contacts the exhaust oxygen sensor, the temperature of the sensor may decrease. The controller may monitor temperature of the exhaust oxygen sensor, and if the temperature of the sensor falls below a threshold temperature, the controller may deduce that water has splashed on the sensor.

In another example, when water splashes on the sensor, heater power of the exhaust oxygen sensor may decrease. If the heater power decreases to a threshold level, then the controller may deduce that water has splashed on the sensor.

In yet another example, when water splashes on the sensor, the heater power of the exhaust oxygen sensor may be automatically increased in order to increase the sensor temperature. In such an example, the controller may monitor the heater power of the exhaust oxygen sensor. If the heater power increases to a certain power output, then the controller may deduce that water has splashed on the sensor.

In still other examples, water contacting the heating element may be indicated when a pumping current of the exhaust oxygen sensor decreases by a threshold current amount. For example, while the exhaust oxygen sensor is operated in the non-VVs mode, the sensor may be operated at a lower voltage, and a corresponding pumping current output may be used to estimate AFR. However, when water splashes on the sensor, the pumping current of the sensor may being to decrease. As such, the pumping current may decrease in response to the reduced oxygen concentration of the air flow (e.g., water splash may cause water vapor surrounding the sensor to reduce the oxygen concentration). When the pumping current of the sensor decreases below the threshold current, the controller may conclude that a water splash event has occurred. As such, water splashing on the sensor may be detected by monitoring the Nernst cell resistance (Rpvs). Herein, the Nernst cell resistance is used to infer the temperature of the sensor. Thus, when Rpvs drops below a threshold resistance, the controller may infer that the temperature of the sensor has fallen below a threshold temperature, and accordingly, determine that water has splashed on the element of the sensor. In another example, water splashing on the sensor may be detected by monitoring oxygen sensor heater resistance. In yet another example, the controller may detect water on the exhaust oxygen sensor based on the pumping current of the sensor in VVs mode. For example, the exhaust oxygen sensor may be operated in the VVs mode wherein exhaust humidity is dissociated. As such, the pumping current Ip of the sensor in the VVs mode may be a base signal corresponding to the amount of oxygen dissociated from the water. When liquid water is present on the exhaust oxygen sensor that is in VVs mode, due to water splash, there will be excess water to dissociate beyond the base level present in the exhaust. Thus, the pumping current signal of the sensor in VVs mode may increase drastically. As such, the high levels of pumping current may only be reached if liquid water was present on the sensor. Therefore, when the pumping current of the exhaust oxygen sensor abruptly increases, the controller may detect water on the sensor.

If water is not detected on the exhaust oxygen sensor (e.g., "NO" at 306), then method 300 proceeds to 310 where it is checked if it is time for a baseline change in pumping current ($\Delta Ip$) measurement. The baseline $\Delta Ip$ value may represent the amount of water in the exhaust gas due to humidity (and/or other water elements in the exhaust gas). In some examples, the controller estimates the baseline $\Delta Ip$ during certain engine operating conditions. As an example, the controller may operate the exhaust oxygen sensor to estimate $\Delta Ip$ at an engine start. As another example, the controller may estimate $\Delta Ip$ periodically (e.g., after a threshold duration of engine operation, a threshold number of engine cycles, and the like).

If it is time for baseline $\Delta Ip$ measurement (e.g., "YES" at 310), then method 300 proceeds to 318. At 318, the controller operates the exhaust oxygen sensor in the VVs mode wherein the sensor is operated at the second, higher voltage and/or modulated between the lower, first voltage and the second, higher voltage. Responsive to modulating the voltage of the exhaust oxygen sensor between the first and second voltages, first and second pumping currents may be generated. The first pumping current may be indicative of an amount of oxygen in a sample gas while the second pumping current may be indicative of the amount of oxygen in the sample gas plus an amount of oxygen contained in water molecules in the sample gas. The controller may find a difference between the first and the second pumping currents to determine the baseline $\Delta Ip$. The baseline $\Delta Ip$ reflects the amount of water that is present in the exhaust gas. This amount of water in the exhaust gas may be due to humidity in the exhaust (and not excess water splashing on the sensor). The controller may store the baseline $\Delta Ip$ in a database to retrieve at a later time, and the method returns.

If it is not time for the baseline $\Delta Ip$ measurement (e.g., "NO" at 310), then method 300 proceeds to 320 where the controller continues to maintain non-VVs operation of the exhaust oxygen sensor. Additionally, the controller may estimate AFR based on the output of the exhaust oxygen sensor, as previously described. Accordingly, the controller may adjust fuel injection to the engine cylinders to maintain overall stoichiometric operation. Method 300 returns.

Returning to 306 of method 300, if the controller deduces that water has splashed on the sensor (e.g., "YES" at 306), then method 300 proceeds to 308 where the sensor is transitioned to the VVs mode. As described previously, the controller may deduce that water has splashed on the exhaust oxygen sensor (or that a water splash event has occurred) based several conditions. The conditions include one or more of the temperature of the exhaust oxygen sensor falling below the threshold temperature, the heater power decreasing to the threshold level, and the pumping current of the sensor falling below the threshold current level, as discussed previously. Accordingly, the controller may transition the exhaust oxygen sensor from the non-VVs mode to the VVS mode wherein the sensor is operated at the second, higher voltage and/or modulated between the lower, first voltage and the second, higher voltage.

Next, at 312, method 300 includes obtaining pumping currents of the exhaust oxygen sensor at the first and the second voltage. Similar to 318 of method 300, the controller may modulate the exhaust oxygen sensor between the first and second voltage and generate a first and a second pumping current at the respective voltages. Additionally, the controller may determine a difference, $\Delta Ip$ between the first and the second pumping currents. Specifically, the $\Delta Ip$ is the change in pumping current when the exhaust oxygen sensor is modulated between the first and the second voltage when water is present on the exhaust oxygen sensor. To differentiate $\Delta Ip$ from the baseline $\Delta Ip$ determined at 318, the $\Delta Ip$ generated at 312 (when water is present on the sensor) will henceforth be referred to as a second $\Delta Ip$.

Next, at 314, the method includes comparing the second $\Delta Ip$ with the first or baseline $\Delta Ip$. To reiterate, the baseline $\Delta Ip$ is the change in pumping current determined by operating the exhaust oxygen sensor in VVs mode when no water is detected on the sensor, and the second $\Delta Ip$ is the change in pumping current determined by operating the exhaust oxygen sensor in VVs mode when water is detected on the sensor. In some example, the baseline $\Delta Ip$ or baseline pumping current of the exhaust oxygen sensor may be referred to as a baseline output of the exhaust oxygen sensor. Herein, the baseline output (or baseline $\Delta Ip$) of the exhaust oxygen sensor is based on an expected amount of oxygen dissociated from water present in the exhaust environment. Therefore, the baseline $\Delta Ip$ represents the base levels of water present in the exhaust. However, when water splashes on the exhaust oxygen sensor, there will be excess water to dissociate beyond the base level of water present in the exhaust.

In one example, the controller may perform actions to accelerate evaporation of water from the exhaust oxygen sensor. For example, the controller may increase heater power to a certain level to accelerate the evaporation of water from the exhaust oxygen sensor. In some cases, operating the sensor in the VVs mode may be used to dissociate the additional water, which may expedite the evaporation since it is dissociating the water present on the sensor. In another example, operating the exhaust oxygen sensor in the VVs mode by modulating the operating voltage between the first and the second voltage may accelerate the evaporation process.

At 316, the controller may determine if the second $\Delta Ip$ is within a threshold amount of the baseline $\Delta Ip$. In one example, if the second $\Delta Ip$ is within 5% or 10% of the baseline $\Delta Ip$, then method 300 proceeds to 332, otherwise, method 300 proceeds to 322. In some examples, the controller may generate a difference, d, between the second and the baseline $\Delta Ip$ to deduce if water is present on the sensor. As an example, the controller may determine the difference d between second and the baseline $\Delta Ip$, and check if the difference d is lower than a threshold value. If the difference d is lower than the threshold value, then the controller may determine that the second $\Delta Ip$ is within the threshold amount of first or baseline $\Delta Ip$ and accordingly, method 300 proceeds to 332. However, if the difference d is higher than the threshold value, the controller may determine that the second $\Delta Ip$ is not within the threshold amount of the baseline $\Delta Ip$, and method 300 proceeds to 322.

At 322, method 300 includes deducing that water is still present on the exhaust oxygen sensor. Thus, the method includes indicating water still present on the exhaust oxygen sensor based the second $\Delta Ip$ not within a threshold of the baseline $\Delta Ip$. Because of the indication, the controller may further adjust one or more sensor operation and engine operation at 324. Adjusting sensor and/or engine operation at 324 includes continuing to operate the exhaust oxygen sensor in the VVs mode at 326. As such, the controller may continue to modulate the exhaust oxygen sensor between the first and the second voltage. In addition, the controller may monitor each of the first and the second pumping current while modulating the sensor between the first and the second voltage. For example, the controller may continue operating the sensor in the VVs mode and keep checking the second $\Delta Ip$ with the baseline $\Delta Ip$ to determine if water is still present on the sensor or if water has evaporated from the sensor. In addition, adjusting sensor and/or engine operation at 324 may include reducing an exhaust gas recirculation (EGR) flow. For example, the controller may decrease an opening of an EGR valve positioned in an EGR passage, to decrease the EGR flow through the exhaust passage. As such, the EGR flow may be reduced to reduce moisture entering the exhaust.

At 328, method 300 includes determining the AFR in the exhaust based on the output of a different sensor. Specifically, the controller may not determine AFR based on the output of the exhaust oxygen sensor. Since the exhaust oxygen sensor still has water present on it, the controller may continue to operate the exhaust oxygen sensor in the VVs mode, and not as a traditional air fuel sensor. However, while the exhaust oxygen sensor is not used as a traditional air fuel sensor, the controller may operate additional sensors coupled to the engine system to determine AFR. As an example, the controller may estimate AFR based on the output of a downstream sensor. The downstream sensor may be a non-limiting example of downstream sensor 128 shown in FIG. 1. As previously described, the downstream sensor may be a linear oxygen sensor or UEGO, a two-state oxygen sensor or EGO, a HEGO (heated EGO), a NOx, HC, or CO sensor. The controller may estimate AFR based on the output of the downstream sensor and not on the exhaust oxygen sensor that still has water present on it. As another example, the controller may estimate AFR based on the output of one or more mass flow sensors and intake manifold pressure sensors coupled to the engine system.

At 330, the controller may adjust fuel injection based on the AFR determined using sensors other than the exhaust oxygen sensor. For example, the controller may determine a control signal to send to the fuel injector actuator, such as a pulse width of the signal, being determined based on a determination of the AFR. The controller may determine the pulse width through a determination that directly takes into account the determined AFR (from downstream sensor, for example), such as increasing the pulse width with decreasing AFR to maintain stoichiometric operation. The controller may alternatively determine the pulse width based on a calculation using a look-up table or an air-fuel ratio map, with the input being AFR and the output being pulse-width. Method 300 returns to 316 to continue monitoring the change in pumping current (or second $\Delta$Ip) and comparing it with baseline change in pumping current (or first $\Delta$I) as discussed earlier. In some examples, the controller may not use additional sensors for estimating AFR. However, the controller may look up the AFR that was estimated using the exhaust oxygen sensor prior to water splashing on the sensor. The controller may use this previously determined AFR to adjust fuel injection at 330.

Returning to 316 of method 300, if the second $\Delta$Ip is within the threshold of the first or baseline $\Delta$Ip (e.g., "YES" at 316), then method 300 proceeds to 332 where method 300 includes deducing that water on the exhaust oxygen sensor has evaporated. Next, at 334, method 300 includes adjusting one or more of sensor operation and engine operation based on the deduction that all the water has evaporated from the exhaust oxygen sensor. Adjusting sensor and/or engine operation includes returning the exhaust oxygen sensor from the VVs mode of operation to the non-VVs or reference mode at 336. Returning the exhaust oxygen sensor to the non-VVs mode includes operating the sensor at the lower voltage, and using the output of the exhaust oxygen sensor in non-VVs mode for estimating AFR at 338. Thus, the exhaust oxygen sensor may be operated at only the first voltage, in the non-VVs mode, in response to a deduction that water has evaporated from the sensor. Herein, the estimated AFR is determined based on an output of the exhaust oxygen sensor operating in the non-VVs mode. In addition, the EGR flow through the EGR passage may be increased. For example, the controller may increase the opening of the EGR valve to increase the EGR flow through the EGR passage based on the deduction that water is no longer present on the sensor. Method 300 returns.

Thus, the example method described above includes, responsive to detecting water on an exhaust oxygen sensor, transitioning the exhaust oxygen sensor from operation in a non-variable voltage (VVs) mode to a VVs mode, and adjusting an engine operating condition in response to an output of the exhaust oxygen sensor during operation in the VVs mode being greater than a baseline output. Additionally or alternatively, the baseline output may include a baseline pumping current of the exhaust oxygen sensor when the exhaust oxygen sensor is operated in the VVs mode when no water is present on the exhaust oxygen sensor. Additionally or alternatively, the baseline output may be based on an expected amount of oxygen dissociated from water present in an exhaust environment. Additionally or alternatively, transitioning the exhaust oxygen sensor from operation in the non-VVs mode to the VVs mode may include transitioning the exhaust oxygen sensor from operating at a first reference voltage to modulating between the first reference voltage and a second reference voltage, the second reference voltage higher than the first reference voltage. Additionally or alternatively, adjusting the engine operating condition may include adjusting fuel injection based on an air flow ratio (AFR) estimated by the exhaust oxygen sensor in the non-VVs mode when no water detected on the exhaust oxygen sensor. Additionally or alternatively, adjusting the engine operating condition may further include adjusting the fuel injection based on the AFR estimated from a different, downstream sensor when water is detected on the exhaust oxygen sensor. In this way, by selectively operating the exhaust oxygen sensor in the VVs mode when water splash event has occurred, sensor degradation may be reduced.

Turning now to FIG. 4, map 400 shows an example relationship between modes of operation of an exhaust oxygen sensor (such as an exhaust oxygen sensor 126 shown in FIG. 1 and/or sensor 200 of FIG. 2), a pumping current output of the exhaust oxygen sensor, a change in baseline pumping current, an air-fuel ratio control, and a fuel injection profile. Plot 402 of map 400 shows the operation of the exhaust oxygen sensor in one of two modes: a non-VVs mode and a VVs mode. Plot 404 shows the pumping current of the exhaust oxygen sensor when operated in the non-VVs mode (e.g., baseline pumping current) and plot 405 shows the pumping current of the sensor in the VVs mode (e.g., at the second pumping current) as described in FIGS. 2 and 3. Plot 408 shows the change in pumping current $\Delta$Ip relative to a baseline $\Delta$Ip (dashed line 410) when the exhaust oxygen sensor is operated in the VVs mode. Plot 412 indicates a water splash event, and shows the amount of water (plot 414) on the exhaust oxygen sensor when the sensor is operated in the VVs mode. Plot 416 shows air-fuel ratio estimated based on the output of the exhaust oxygen sensor (e.g., UEGO), and plot 426 shows AFR estimated using a different, downstream sensor (e.g., HEGO). Plot 418 shows fuel injection profiles based on AFR estimated using both the exhaust oxygen sensor and the downstream sensor, and plot 420 shows fuel injection profiles based on AFR estimated using only the downstream sensor. For each plot, time is depicted along the x (horizontal) axis while values of each respective parameter are depicted along the y (vertical) axis.

Between time t0 and t1, the exhaust oxygen sensor is operated as a traditional air-fuel sensor. Hence, the exhaust oxygen sensor is operated in the non-VVs mode (402) where the sensor is operated in a lower voltage as described in FIG. 2. In the non-VVs mode, the pumping current (404) of the exhaust oxygen sensor is used to estimate AFR (416). In some examples, the pumping current (404) may represent a first pumping current of the exhaust oxygen sensor when the sensor is operated at the first (lower) voltage. As an example, when the air/fuel mixture is rich the exhaust oxygen sensor produces a pumping current (404) in the "negative" direction to consume free fuel. When the air/fuel mixture is lean, the exhaust oxygen sensor produces a pumping current in the opposite ("positive") direction to consume free oxygen. In this way, the exhaust oxygen sensor may be used to estimate AFR. Based on the AFR estimated using the pumping current of the exhaust oxygen sensor, fuel injection profile (418) may be adjusted in order to maintain stoichiometric operation. In some examples, the fuel injection profile (418) may be adjusted based on one or more exhaust oxygen sensor and a different, downstream sensor. As previously described, the engine system may include additional sensors mounted along the exhaust passage, which may be used for AFR estimation. For example, a HEGO sensor may be placed downstream of an emission device, and the output of the HEGO sensor may be used in addition to the output of the exhaust oxygen sensor to determined fuel injection profile (418). In one example, the controller may estimate an AFR based on an average of the AFR estimated from the UEGO sensor and the HEGO sensor. In another example, the controller may use the AFR estimated from the HEGO as a correction factor to the AFR estimated from the UEGO sensor, and apply the corrected AFR for air-fuel control. In yet another example, the UEGO sensor may provide feedback to adjust the AFR near stoichiometry, and the HEGO sensor may provide feedback to bias the AFR richer or leaner to enhance catalyst efficiency. For example, the upstream exhaust oxygen sensor (UEGO) may be operated in a manner to control an inner loop of the AFR, and the downstream oxygen sensor (HEGO) may be operated in a manner to control an outer loop of the AFR. The HEGO sensor may be used to apply corrections to the UEGO's AFR ratio measurement and may thus maintain proper rich vs. lean state of the catalyst.

Between time t1 and t2, the pumping current (404) of the exhaust oxygen sensor starts decreasing. Herein, the pumping current (404) may be referred to as the baseline pumping current of the exhaust oxygen sensor in non-VVs mode when no water id detected on the sensor. At time t2, the pumping current falls below a first threshold current (dashed line 407). When this occurs, a water splash event (412) is detected. As such, water may splash on the exhaust oxygen sensor, causing the baseline pumping current to fall below the first threshold current. Herein, the first threshold current is based on the first output or pumping current (404) of the exhaust oxygen sensor in the non-VVs or reference mode when no water is present on the exhaust oxygen sensor. In some examples, water splash event may be detected based on a temperature of the sensor falling below a threshold temperature.

If the exhaust oxygen sensor is continued to be operated in the non-VVs mode even after water splash is detected, the sensor may get degraded. In order to reduce sensor degradation, the exhaust oxygen sensor may no longer be operated in the non-VVs mode. Instead, the exhaust oxygen sensor may be transitioned from the non-VVs mode to the VVs mode (402) at time t2. Thus, between t2 and t3, the exhaust oxygen sensor is operated in the VVs mode where the sensor is modulated between a lower, first and a higher, second voltage. As the sensor is modulated between the first and the second voltage, the sensor generates a first and a second pumping current at the respective voltages. Herein, the raw pumping current output (either first or the second pumping current) is shown in plot 405, and a difference between the second pumping current and the first pumping current is shown in plot 408.

In the VVs mode, AFR may not be determined using the exhaust oxygen sensor output (see flat line 416 between t2 and t3). Nevertheless, AFR may be estimated using the downstream sensor (426) and fuel injection profile (420) may be adjusted based on the AFR (426) estimated from the downstream sensor.

If downstream sensor is not available, then the fuel injection profile (420) may be adjusted between pre-determined thresholds (422 and 424). For example, a lower threshold (424) and an upper threshold (422) may be determined based on a previously estimated AFR when the exhaust oxygen sensor was operated in the non-VVs mode (e.g., between t0 and t1). Between t2 and t3, the fuel injection profile (420) may be adjusted between the previously determined upper and lower thresholds.

Thus, upon detecting water on the exhaust oxygen sensor, the sensor may not be operated as a traditional air-fuel sensor. Instead, the sensor may be transitioned to the VVs mode and in some examples, the sensor may be operated to estimate ambient humidity. In response to modulating the voltage of the exhaust oxygen sensor between the first and second voltages, the first and second pumping currents may be generated. The first pumping current may be indicative of an amount of oxygen in a sample gas while the second pumping current may be indicative of the amount of oxygen in the sample gas plus an amount of oxygen contained in water molecules (added due to water splash) in the exhaust gas. Thus, a change in pumping current $\Delta I_p$ (408) may be determined by subtracting the first pumping current from the second pumping current. As such, the change in pumping current $\Delta I_p$ (408) may be compared with the baseline change in pumping current (410). As described previously, the baseline $\Delta I_p$ (410) may be determined during certain engine operating conditions (e.g., during an engine start, or after a threshold duration of engine operation or after a threshold number of engine cycles). Between t2 and t3, the change in pumping current (408) is higher than the baseline $\Delta I_p$ (410), therefore indicating that water is still present at the exhaust oxygen sensor (as indicated by the amount of water present at the sensor by plot 414).

Water on the exhaust oxygen sensor may begin to evaporate (as indicated by plot 414). At t3, the change in pumping current (408) reaches the baseline $\Delta I_p$ (410), indicating that the water levels in the exhaust is substantially equal to the baseline levels of water expected to be present in the exhaust. Thus, at t3, it may be concluded that water has evaporated from the sensor (or the water on sensor is substantially equal to expected water levels in the exhaust), and the accordingly, the exhaust oxygen sensor may be returned to the non-VVs mode, where it is operated as a traditional air-fuel sensor. Thus, between t3 and t4, the exhaust oxygen sensor may be used to estimate AFR (416) and based on the estimated AFR, fuel injection profile (418) may be accordingly adjusted.

In some examples, instead of using the change in pumping current, the controller may use the raw pumping current values to determine if water is still present on the sensor. For example, the raw pumping current (405) of the exhaust oxygen sensor at one or more the first, lower voltage and the second, higher voltage may be monitored between t2 and t3. While the sensor is modulated between the first voltage and the second voltage in the VVs mode between time t2 and t3, instead of calculating a difference between the first and the second pumping current, the raw pumping current value may be used to detect if water is still detected on the sensor. In one example, the raw pumping current may include an average of the first pumping current (at first voltage) and the second pumping current (at the second voltage). The baseline pumping (404) current of the sensor in non-VVs mode may be indicative of an amount of oxygen in a sample gas while the raw pumping current (405) of the sensor in VVs mode may be indicative of the amount of oxygen in the sample gas plus an amount of oxygen contained in water molecules (added due to water splash) in the exhaust gas.

For example, between time t2 and t3, the second pumping current (405) is above a second threshold current (dashed line 406). This indicates that water is still present on the sensor. Herein, the first threshold current (407) is based on a first output of the sensor in the non-VVs mode when no water is present on the sensor, and the second threshold current (406) is based on a second output of the sensor in the VVs mode when water is present on the sensor. As shown in map 400, the second threshold current (406) is higher than the first threshold current (407). Thus, when the second pumping current (405) is higher than the second threshold current (406), the controller may deduce that water is still present on the sensor.

However, at t3, when the second pumping current (405) falls below the second threshold current (406), indicating that water is no longer present on the sensor. As discussed previously, the exhaust oxygen sensor may be transitioned back to the non-VVs mode where it functions as a traditional air-fuel sensor. Thus, between t3 and t4, the exhaust oxygen sensor may be used to estimate AFR (416) and based on the estimated AFR, fuel injection profile (418) may be accordingly adjusted.

In this way, by operating the exhaust oxygen sensor in the VVs mode when water is present on the sensor, sensor degradation may be reduced. The technical effect of transitioning the sensor from the non-VVs mode to the VVs mode when water is detected is that the sensor parameter in the VVs mode is used to determine when the water has evaporated from the sensor. Thus, sensor degradation may be avoided. In addition, the sensor may not be used to determine AFR when water is still present on the exhaust oxygen sensor, instead AFR may be estimated from a different sensor. In this way, air-fuel control of the engine system may be maintained.

The systems and methods described above provide for a method comprising indicating water at an exhaust oxygen sensor positioned in an engine exhaust passage based on a sensor parameter of the exhaust oxygen sensor while operating the exhaust oxygen sensor in a variable voltage (VVs) mode where a reference voltage is adjusted from a lower, first voltage to a higher, second voltage, and adjusting one or more of sensor operation and engine operation based on the indicating water. In a first example of the method, the method may additionally or alternatively include wherein the sensor parameter includes a change in pumping current when the exhaust oxygen sensor is modulated between the first voltage and the second voltage. A second example of the method optionally includes the first example, and further includes wherein the sensor parameter includes a pumping current of the exhaust oxygen sensor when the exhaust oxygen sensor is operated at the second voltage. A third example of the method optionally includes one or more of the first and the second examples, and further includes indicating water at the exhaust oxygen sensor in response to the pumping current of the exhaust oxygen sensor being higher than a threshold current, and wherein the adjusting the exhaust oxygen sensor operation includes operating the exhaust oxygen sensor in the VVs mode until the pumping current falls below the threshold current. A fourth example of the method optionally includes one or more of the first through the third examples, and further includes indicating no water at the exhaust oxygen sensor once the pumping current falls below the threshold current, and wherein the adjusting the exhaust oxygen sensor operation includes transitioning the exhaust oxygen sensor from the VVs mode to a non-VVs mode where the reference voltage is adjusted to and maintained at the first voltage. A fifth example of method optionally includes one or more of the first through the fourth examples, and further includes wherein the threshold current is based on a baseline pumping current, the baseline pumping current determined based on an output of the exhaust oxygen sensor while operating in the VVs mode when no water is detected at the sensor. A sixth example of method optionally includes one or more of the first through the fifth examples, and further includes wherein adjusting one or more of the sensor operation and the engine operation includes reducing an exhaust gas recirculation (EGR) flow responsive to the pumping current of the exhaust oxygen sensor being higher than the threshold current. A seventh example of method optionally includes one or more of the first through the sixth examples, and further includes wherein the adjusting one or more of the sensor operation and the engine operation further includes increasing the EGR flow responsive to the pumping current of the exhaust oxygen sensor falling below the threshold current. An eighth example of method optionally includes one or more of the first through the seventh examples, and further includes wherein reducing the EGR flow includes decreasing an opening of an EGR valve positioned in an EGR passage, and increasing the EGR flow includes increasing the opening of the EGR valve.

The systems and methods described above also provide for a method comprising responsive to detecting water on an exhaust oxygen sensor, transitioning the exhaust oxygen sensor from operation in a non-variable voltage (VVs) mode to a VVs mode, and adjusting an engine operating condition in response to an output of the exhaust oxygen sensor during operation in the VVs mode being greater than a baseline output. In a first example of the method, the method may additionally or alternatively include wherein the baseline output includes a baseline pumping current of the exhaust oxygen sensor when the exhaust oxygen sensor is operated in the VVs mode when no water is present on the exhaust oxygen sensor. A second example of the method optionally includes the first example, and further includes wherein the baseline output is based on an expected amount of oxygen dissociated from water present in an exhaust environment. A third example of the method optionally includes one or more of the first and the second examples, and further includes wherein transitioning the exhaust oxygen sensor from operation in the non-VVs mode to the VVs mode includes transitioning the exhaust oxygen sensor from operating at a first reference voltage to modulating between the first reference voltage and a second reference voltage, the second reference voltage higher than the first reference voltage. A fourth example of the method optionally includes one or more of the first through the third examples, and further includes wherein adjusting the engine operating condition includes adjusting fuel injection based on an air flow ratio (AFR) estimated by the exhaust oxygen sensor in the non-VVs mode when no water detected on the exhaust oxygen sensor. A fifth example of method optionally includes one or more of the first through the fourth examples, and further includes wherein adjusting the engine operating condition further includes adjusting the fuel injection based on the AFR estimated from a different, downstream sensor when water is detected on the exhaust oxygen sensor.

The systems and methods described above provide for a system for an engine, comprising an exhaust oxygen sensor coupled to an exhaust passage of the engine, and a controller including computer readable instructions for during operation of the exhaust oxygen sensor in a reference mode where a reference voltage of the exhaust oxygen sensor is maintained at a lower, first voltage, detecting a water splash event based on a first pumping current of the exhaust oxygen sensor falling below a first threshold current, and transitioning the exhaust oxygen sensor to a variable voltage (VVs) mode where the reference voltage is modulated between the first voltage and a higher, second voltage and maintaining operation in the VVs mode until a second pumping current of the exhaust oxygen sensor falls below a second threshold current, the second pumping current generated at one or more of the first voltage and the second voltage. In a first example of the system, the system may additionally or alternatively include wherein the first threshold current is based on a first output of the exhaust oxygen sensor in the reference mode when no water is present on the exhaust oxygen sensor, and the second threshold is based on a second output of the exhaust oxygen sensor in the VVs mode when water is present on the exhaust oxygen sensor. A second example of the system optionally includes the first example, and further includes wherein the second threshold current is higher than the first threshold current. A third example of the system optionally includes one or more of the first and the second examples, and further includes wherein the controller includes instructions for estimating an air-fuel ratio based on the first output of the exhaust oxygen sensor when operating the exhaust oxygen sensor in the reference mode. A fourth example of the system optionally includes the first through the third examples, and further includes wherein the controller includes instructions for estimating ambient humidity based on the second output of the exhaust oxygen sensor when operating the exhaust oxygen sensor in the VVs mode.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An engine method, comprising:
indicating water at an exhaust oxygen sensor positioned in an engine exhaust passage based on a sensor parameter of the exhaust oxygen sensor while operating the exhaust oxygen sensor in a variable voltage (VVs) mode where a reference voltage is adjusted from a lower, first voltage to a higher, second voltage;
adjusting one or more of sensor operation and engine operation based on the indicating water, wherein the sensor parameter includes a pumping current of the exhaust oxygen sensor when the exhaust oxygen sensor is operated at the second voltage; and
indicating water at the exhaust oxygen sensor in response to the pumping current of the exhaust oxygen sensor being higher than a threshold current, and wherein the adjusting the exhaust oxygen sensor operation incudes operating the exhaust oxygen sensor in the VVs mode until the pumping current falls below the threshold current.

2. The method of claim 1, wherein the sensor parameter includes a change in pumping current when the exhaust oxygen sensor is modulated between the first voltage and the second voltage.

3. The method of claim 1, further comprising indicating no water at the exhaust oxygen sensor once the pumping current falls below the threshold current, and wherein the adjusting the exhaust oxygen sensor operation includes transitioning the exhaust oxygen sensor from the VVs mode to a non-VVs mode where the reference voltage is adjusted to and maintained at the first voltage.

4. The method of claim 1, wherein the threshold current is based on a baseline pumping current, the baseline pumping current determined based on an output of the exhaust oxygen sensor while operating in the VVs mode when no water is detected at the exhaust oxygen sensor.

5. The method of claim 1, wherein adjusting one or more of the sensor operation and the engine operation includes reducing an exhaust gas recirculation (EGR) flow responsive to the pumping current of the exhaust oxygen sensor being higher than the threshold current.

6. The method of claim 5, wherein the adjusting one or more of the sensor operation and the engine operation further includes increasing the EGR flow responsive to the pumping current of the exhaust oxygen sensor falling below the threshold current.

7. The method of claim 6, wherein reducing the EGR flow includes decreasing an opening of an EGR valve positioned in an EGR passage, and increasing the EGR flow includes increasing the opening of the EGR valve.

8. A method comprising:
responsive to detecting water on an exhaust oxygen sensor, transitioning the exhaust oxygen sensor from operation in a non-variable voltage (VVs) mode to a VVs mode; and
adjusting an engine operating condition in response to an output of the exhaust oxygen sensor during operation in the VVs mode being greater than a baseline output, wherein the baseline output includes a baseline pumping current of the exhaust oxygen sensor when the exhaust oxygen sensor is operated in the VVs mode when no water is detected on the exhaust oxygen sensor.

9. The method of claim 8, wherein the baseline output is based on an expected amount of oxygen dissociated from water present in an exhaust environment.

10. The method of claim 8, wherein transitioning the exhaust oxygen sensor from operation in the non-VVs mode to the VVs mode includes transitioning the exhaust oxygen sensor from operating at a first reference voltage to modulating between the first reference voltage and a second reference voltage, the second reference voltage higher than the first reference voltage.

11. The method of claim 8, wherein adjusting the engine operating condition includes adjusting fuel injection based on an air flow ratio (AFR) estimated by the exhaust oxygen sensor in the non-VVs mode in response to no water being detected on the exhaust oxygen sensor.

12. The method of claim 11, wherein adjusting the engine operating condition further includes adjusting the fuel injection based on the AFR estimated from a different, downstream sensor in response to water being detected on the exhaust oxygen sensor.

13. A system for an engine, comprising:
an exhaust oxygen sensor coupled to an exhaust passage of the engine; and
a controller including computer readable instructions stored in memory for:
during operation of the exhaust oxygen sensor in a reference mode where a reference voltage of the exhaust oxygen sensor is maintained at a lower, first voltage, detecting a water splash event based on a first pumping current of the exhaust oxygen sensor falling below a first threshold current; and
transitioning the exhaust oxygen sensor to a variable voltage (VVs) mode where the reference voltage is modulated between the first voltage and a higher, second voltage and maintaining operation in the VVs mode until a second pumping current of the exhaust oxygen sensor falls below a second threshold current, the second pumping current generated at one or more of the first voltage and the second voltage.

14. The system of claim 13, wherein the first threshold current is based on a first output of the exhaust oxygen sensor in the reference mode when no water is present on the exhaust oxygen sensor, and the second threshold current is based on a second output of the exhaust oxygen sensor in the VVs mode when water is present on the exhaust oxygen sensor.

15. The system of claim 13, wherein the second threshold current is higher than the first threshold current.

16. The system of claim 14, wherein the controller includes instructions for estimating an air-fuel ratio based on the first output of the exhaust oxygen sensor when operating the exhaust oxygen sensor in the reference mode.

17. The system of claim 14, wherein the controller includes instructions for estimating ambient humidity based on the second output of the exhaust oxygen sensor when operating the exhaust oxygen sensor in the VVs mode.

* * * * *